US012594116B2

(12) United States Patent
   Bohnsack

(10) Patent No.: US 12,594,116 B2
(45) Date of Patent: Apr. 7, 2026

(54) METHOD FOR TREATING CHRONIC RHINITIS

(71) Applicant: OLYMPUS WINTER & IBE GMBH, Hamburg (DE)

(72) Inventor: Claudia Alexandra Bohnsack, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 771 days.

(21) Appl. No.: 17/872,770

(22) Filed: Jul. 25, 2022

(65) Prior Publication Data

US 2023/0034335 A1      Feb. 2, 2023

Related U.S. Application Data

(60) Provisional application No. 63/226,239, filed on Jul. 28, 2021.

(51) Int. Cl.
| | |
|---|---|
| *A61B 18/14* | (2006.01) |
| *A61B 18/00* | (2006.01) |
| *A61B 18/12* | (2006.01) |

(52) U.S. Cl.
CPC ... *A61B 18/1485* (2013.01); *A61B 2018/00327* (2013.01); *A61B 2018/00434* (2013.01); *A61B 2018/00875* (2013.01); *A61B 2018/1253* (2013.01); *A61B 2018/126* (2013.01)

(58) Field of Classification Search
CPC ...... A61B 18/1485; A61B 2018/00327; A61B 2018/00434; A61B 2018/00875; A61B 2018/1253; A61B 2018/126; A61B 2018/1465; A61B 2018/1467; A61B 2018/147
USPC .... 606/41, 42, 47–52; 607/98, 99, 101, 113, 607/115, 116, 135
See application file for complete search history.

(56) References Cited

U.S. PATENT DOCUMENTS

| | | | | |
|---|---|---|---|---|
| 7,468,060 B2 * | 12/2008 | Utley | ...................... | A61F 5/005 606/41 |
| 2005/0240147 A1 * | 10/2005 | Makower | ............. | A61B 18/042 623/1.11 |
| 2019/0343577 A1 * | 11/2019 | Wolf | .................. | A61B 18/1485 |
| 2021/0236199 A1 * | 8/2021 | Frazier | ............... | A61B 18/1206 |

* cited by examiner

*Primary Examiner* — Thomas A Giuliani
(74) *Attorney, Agent, or Firm* — OLIFF PLC

(57) ABSTRACT

A method for treating patients who suffer from chronic rhinitis that is efficient and causes fewer adverse effects than known methods. This is achieved by using a handheld surgical instrument, more particularly an electrosurgical applicator, for treatment of hypertrophic nasal conchae and/or for submucosal treatment of the posterior nasal nerve (PNN) in order to reduce at least one cardinal symptom of chronic rhinitis.

2 Claims, No Drawings

METHOD FOR TREATING CHRONIC RHINITIS

This application claims the benefit of U.S. Provisional Patent Application No. 63/226,239 filed on Jul. 28, 2021. The disclosure of the prior applications is hereby incorporated by reference herein in its entirety.

The invention relates to a method for treating chronic rhinitis according to claim 1.

Chronic rhinitis (inflammation of the nasal mucosa) encompasses allergic rhinitis, non-allergic rhinitis and mixed subtypes. Although the clinical presentation may vary, a runny nose and nasal congestion are the predominant symptoms which impair a patient's quality of life and motivate the patient to carry out a treatment.

Medical treatments for chronic rhinitis are regarded as the first choice. However, not all patients respond appropriately to the medicinal treatments that are available, and it is for this reason that a procedural intervention or surgical procedure may be necessary for recurrent chronic rhinitis. Classically, the method of choice for refractory rhinitis has been Vidian neurectomy, whereas more recent studies describe the importance of posterior nasal neurectomy. Multiple current reviews have studied the evidence base for the surgical treatment of chronic rhinitis.

Although Vidian neurectomy appears to be effective, there are multiple disadvantages or significant adverse effects, namely possible nasal and ocular morbidity and also the increased costs and resources associated, for example, with the general anaesthesia and the surgical procedure.

The pathophysiology of chronic rhinitis is complex and includes both sensory and autonomic neural pathways. Sensory pathways recognize specific allergens or irritants, which stimulate a parasympathetic response via the Vidian nerve. It has been demonstrated that methods such as Vidian neurectomy can reduce the symptoms of chronic rhinitis. However, adverse effects such as dry eyes owing to the ablation of the parasympathetic innervation of the lachrymal glands may be found. It is assumed that the ablation of the posterior nasal nerve can reduce the adverse effects of dry eyes that occur with a Vidian neurectomy. Therefore, specific therapies which lead to alleviation of the symptoms of chronic rhinitis together with limited adverse effects are pursued in this region.

Cryotherapy has attracted interest because it is simple to carry out by a public health officer. In cryotherapy, liquid nitrogen is used for ablation of the posterior nasal tissue. In cryotherapy, the extremely low temperature of the liquid nitrogen leads to the formation of ice crystals which induce cellular contraction in order to ultimately lyse cells.

Another way to ablate the posterior nasal nerve (PNN) is the use of HF or RF energy or current. In the case of this type of energy, the tissue is heated rather than frozen. An instrument for RF ablation of the PNN is, for example, described in the patent application US 2019/0239957.

Not all patients respond to the treatment methods currently in use, or they suffer from the adverse effects associated with the methods. In the European Union, between 44 and 76 million people out of 217 million employed people in the EU suffer from an allergic disorder of the respiratory tract. Up to 90% of these individuals are untreated or inadequately treated. In Hong Kong, Malaysia, the Philippines, Singapore, Thailand and Vietnam, about 30-53 million people out of the 151 million people in employment suffer from allergic rhinitis. It is estimated that about 90% of patients who suffer from these allergic disorders are inadequately treated, which affects the socioeconomic burden in the form of loss of working hours and reduced productivity.

The surgical treatment of the presently described disorder by means of Vidian neurectomy may cause dry eyes as a side effect due to reduced lachrymal fluid. Further complications may be neurotrophic keratopathy, eye movement disorders, or even blindness.

In the case of the known cryotreatment, use is made of appropriate cryotherapy instruments in order to produce very low temperatures using liquid nitrogen. However, during the freezing process, the instrument does not receive any feedback about the effect of the treatment on the tissue. An adjustment of the treatment or an adjustment to the temperature or the application time is therefore not possible. "Frozen brain syndrome" and only partial resolution of symptoms have been reported by patients following treatment.

In the case of one of multiple known treatment options that use an RF current, use is made of appropriate RF instruments. Such RF instruments or RF probes can comprise an arrangement of small electrodes positioned on a plurality of minute wires. The applicator additionally requires its own RF generator. The generator must be capable of supplying the electrodes of the electrode arrangement with electrical energy. In this connection, the generator must have a specific multi-pole socket for connection of the various electrode pairs. With this type of treatment, there is a tendency for the tissue to come into contact with the small electrodes on the wires during the application of RF energy and to dry out rapidly, thereby reducing therapeutic efficacy.

An alternative known instrument for electrosurgical or RF treatment comprises a handle, a shaft and a treatment tip. Biopolar electrodes can be arranged on this electrically non-conductive tip. A temperature sensor for monitoring tissue temperature can be located on the tip. This instrument treats the symptoms of chronic rhinitis through the use of low doses of HF or RF energy to destroy the tissue in the posterior regions of the nasal nerve. The low-output HF or RF energy generates heat within the submucosal tissue. Since the tip is positioned on the outer surface of the nasal concha, and thus directly on the mucosa, this treatment leads to destruction of the mucosa.

Chronic rhinitis is usually described with three or four cardinal symptoms, namely aqueous rhinorrhoea (nasal discharge), nasal congestion, itchy nose and an urge to sneeze, the first two symptoms being the most common. The instruments currently available only treat one of these symptoms of chronic rhinitis. At the same time, an external approach is used, in which the mucosal tissue is damaged.

It is therefore an object of the present invention to provide a method for treating patients who suffer from chronic rhinitis that is efficient and causes fewer adverse effects than the known methods described.

A method to achieve this object is described by the measures of claim 1. Accordingly, use is made of a handheld surgical instrument, more particularly an electrosurgical applicator, for treatment of hypertrophic nasal conchae and/or for submucosal treatment of the posterior nasal nerve (PNN) in order to reduce at least one cardinal symptom of chronic rhinitis.

Preferably, the method according to the invention is carried out submucosally Through this treatment, the mucosa, which is essential for performing various functions within the nasal cavity such as filtration of air, humidification and temperature adjustment, etc., can be kept intact and the adverse effects of the treatment can thus be reduced.

The use of an individual instrument for the treatment of the two main symptoms rhinorrhoea and nasal congestion can reduce treatment costs, increase comfort for the patient, and reduce the time taken off by workers. Furthermore, this method can treat both symptoms equally as a result of the improvement in air flow. Whereas size-reduction of the nasal concha has a direct influence on the improvement in air flow by solving the problem of nasal congestion, the treatment also reduces nasal discharge at least indirectly. The best possible result can therefore be achieved by this combination of the two methods. Besides this indirect effect, the nasal nerve is also directly restricted in its action submucosally as a result of ablation.

This method can be carried out by using an electrosurgical HF or RF applicator. This applicator, which is monopolar or bipolar, comprises a long shaft with an "acicular" applicator tip at the distal end. One electrode or two electrodes is/are arranged at the tip of the applicator. In the case of the exemplary embodiment of a bipolar applicator, the two electrodes are separated from one another by an insulator. The two electrodes are supplied with an electric current provided by an HF or RF generator. The RF or HF field, which is formed between the two electrodes, leads to heating of the surrounding tissue. As a result of this thermal energy being supplied, the tissue can be coagulated in a specific manner. Both by varying the thermal energy and by appropriately positioning the probe or the applicator tip, it is possible to carry out the above-described treatment with great accuracy and reliability.

In the case of the size-reduction of hypertrophic nasal conchae, the entire length of the inferior nasal concha is treated in the manner just described. This involves starting at the posterior end of the inferior nasal concha, at which the posterior nasal nerve (PNN) is also located.

The method according to the invention is based, inter alia, on the fact that the posterior end of the inferior nasal concha is supplied with HF or RF energy or thermal energy to an increased extent in order to damage the PNN, which is responsible for the increased uncontrolled nasal discharge. Due to the fact that, when the applicator is pulled out of the nasal concha, the method is continued over the entire length, nasal congestion can be treated in the same procedure. It is therefore unnecessary to perform a further procedure for the nasal congestion.

The course or progress of the method can be monitored via impedance feedback. To this end, the impedance of the tissue to be treated is determined continuously or in cycles/periodically via the applicator. By means of the impedance value thus determined, a clear statement can be made about the course of the treatment.

The advantage resulting from this treatment, that two methods are combined together, is that two main symptoms of chronic rhinitis are treatable at the same time, i.e. with the same procedure. In addition, this treatment makes it possible to achieve a direct and indirect improvement in nasal discharge. Lastly, the nasal mucosa can be maintained owing to the completely submucosal approach.

The invention claimed is:

1. A method for treating chronic rhinitis with an electrosurgical HF or RF applicator comprising two electrodes supplied with HF or RF energy via an appropriate generator, the method comprising:
   performing a treatment submucosally;
   coagulating tissue with the electrosurgical HF or RF applicator, the electrosurgical HF or RF applicator being one of a monopolar electrosurgical HF or RF applicator and a bipolar electrosurgical HF or RF applicator;
   generating thermal energy within the tissue by applying one of a HF or a RF field between the two electrodes;
   starting the treatment at a posterior end of an inferior nasal concha, at which a posterior nasal nerve is also located, to treat uncontrolled nasal discharge;
   continuing the treatment as the electrosurgical HF or RF applicator is pulled out along an entire length of the inferior nasal concha, to treat nasal congestion, such that the treatment of the uncontrolled nasal discharge and the nasal congestion is performed in a single treatment step using the electrosurgical HF or RF applicator; and
   monitoring progress of the treatment via impedance feedback, wherein the posterior end of the inferior nasal concha is supplied with HF or RF energy to an increased extent in order to damage the posterior nasal nerve.

2. The method for treating the chronic rhinitis according to claim 1, wherein the treatment of a hypertrophic nasal concha is carried out over the entire length of the inferior nasal concha.

* * * * *